Figure 1:
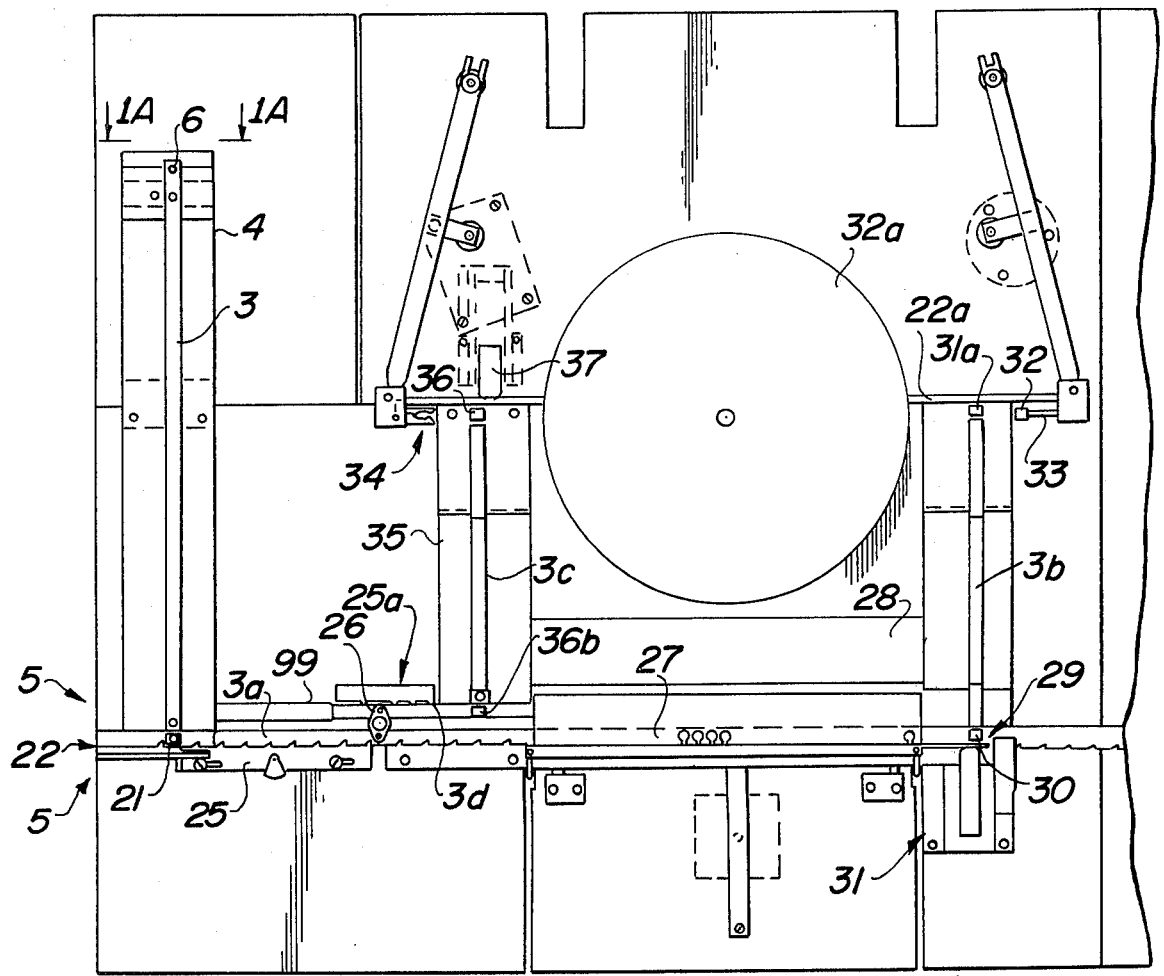

United States Patent [19]

Revillet et al.

[11] 4,022,579
[45] May 10, 1977

[54] TRANSPORT SYSTEM FOR ANALYTICAL EQUIPMENT

[75] Inventors: Georges Revillet, Onex; Manuel C. Sanz, Grand-Lancy; Andre Nicole, Puplinge, all of Switzerland

[73] Assignee: Micromedic Systems, Inc., Horsham, Pa.

[22] Filed: Nov. 12, 1975

[21] Appl. No.: 631,256

[52] U.S. Cl. .................................. 23/259; 23/292; 211/74
[51] Int. Cl.² ..................... B01L 9/06; B01L 11/00
[58] Field of Search ................. 23/259, 292, 253 R; 211/74; 238/130

[56] References Cited

UNITED STATES PATENTS

| | | | |
|---|---|---|---|
| 2,741,913 | 4/1956 | Dovas | 211/74 X |
| 3,489,521 | 1/1970 | Buckle et al. | 23/259 X |
| 3,605,829 | 9/1971 | Genese et al. | 23/259 UX |
| 3,778,232 | 12/1973 | McMorrow, Jr. | 23/259 X |
| 3,812,597 | 5/1974 | Perilhou et al. | 23/259 X |
| 3,897,216 | 7/1975 | Jones | 23/259 |
| 3,916,157 | 10/1975 | Roulette et al. | 23/259 X |
| 3,917,455 | 11/1975 | Bak et al. | 23/259 X |

*Primary Examiner*—Joseph Scovronek

[57] ABSTRACT

A guide rail or track system for guiding test tube holders or racks from one station to another, e.g., in a mono-channel analyzer, for presenting test tubes in such holders in sequence to one or more servicing operations at a plurality of stations. The rail system may comprise a main linear guide rail along which a holder having a row of test tubes supported therein is adapted to be moved longitudinally stepwise to present each test tube in the holder in sequence to a given station, or a given position therein, where an operation is to be carried out with respect to each test tube as it is presented in the station. Arranged at right angles to the main rail, one or more branch rails leading to or from other service stations are provided at spaced intervals and the main rail at each juncture or intersection of these rails is constructed to allow a lateral shift of the holder (also specially constructed to allow such shift) to or from the main rail respectively from or to the branch rail along which the holder moves laterally, i.e., the lengthwise dimension of the holder extends across the branch rail at right angles to it as the test tube holder moves along the branch rail, which may terminate at a junction or intersection with another or subsidiary rail or guideway along which the holder moves longitudinally in a direction parallel to the main rail. Means is provided for moving the holder along the main rail and means is provided at the junction of a branch rail with an intersecting rail such as the main rail, for laterally shifting the holder from the junction.

13 Claims, 11 Drawing Figures

TRANSPORT SYSTEM FOR ANALYTICAL EQUIPMENT

DESCRIPTION OF THE INVENTION

The present invention is concerned with analytical equipment, especially with a rail system for transporting test tube holders or racks therein to one or more "servicing" stations for storage, transfer, dilution, reagent addition, agitating, centrifugation, incubation, spectroscopic analysis, etc. to determine the content of one or more components of a liquid material. The present invention is concerned with a transport system adapted for use in an instrument wherein a multiplicity of liquid samples is carried through the instrument by means of one or more test tube holders or racks. The improved holder of the present invention has a plurality of receptacles, each adapted to receive a test tube, arranged longitudinally of the holder. The holder is provided with a guide structure along its base by which the holder may be moved longitudinally along a track or rail and which is so constructed as to maintain the holder in upright position at all times during the travel of the holder in the equipment. The guide means is so constructed as to allow the transverse motion of the holder laterally from one such track onto another track of similar construction, but extending perpendicularly to the first track, such lateral shifting being accomplished at points along the track provided with appropriate cooperating guide means for lateral motion. The holder is provided with elastic gripping means adapted to grip a test tube inserted into any or all of the receptacles in the holder. The holder is also constructed to allow the insertion of rods or pins either from the top or from below the holder at any selected stage of the instrument to force the test tubes within the holder downwardly so that they protrude below the holder or are lifted upwardly therein or therefrom.

The system of the present invention provides a plurality of tracks or rails along which the holders are adapted to be moved or guided into a series of service stations in the analytical equipment or instrument. For example, a rail or track may be provided which may serve as a supply ramp along which one or more holders for test tubes, either empty or having the liquids to be tested therein, are introduced to the instrument or to a particular stage of the instrument. Means is provided at one end of such a ramp to advance the holder(s) along the rail to a given stage of the instrument after which the holders or holders in succession are advanced to succeeding stages for addition of a reagent, vortexing, dilution, transfer of sample, centrifuging, incubation and/or analyzing a reaction product, supernatant product, or the like, e.g., by photometric measurement.

Figure 1A:
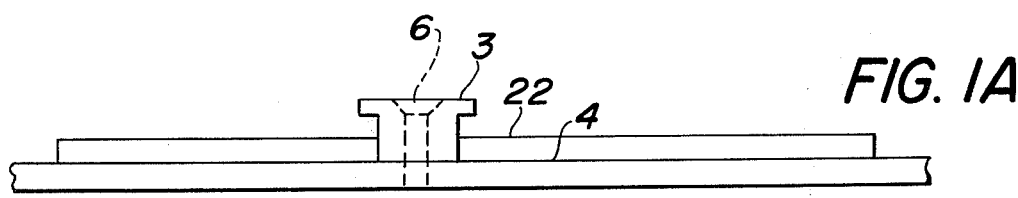
Figure 1B:
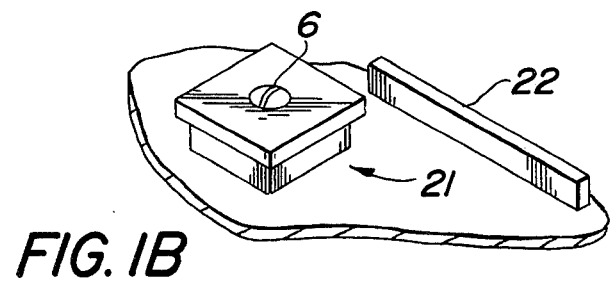
Figure 2:
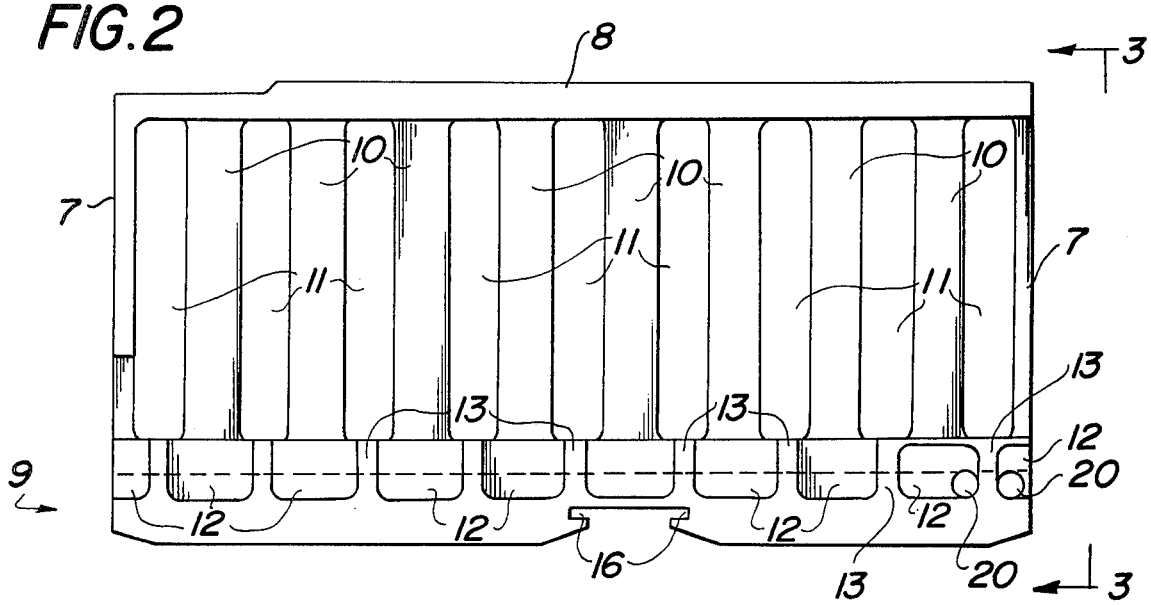
Figure 3:
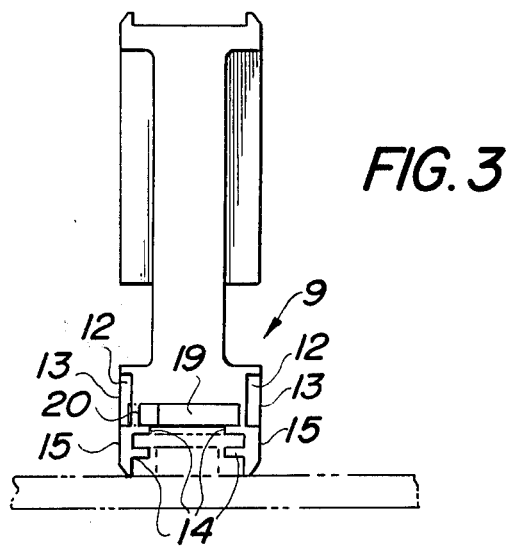
Figure 4:
Figure 5:
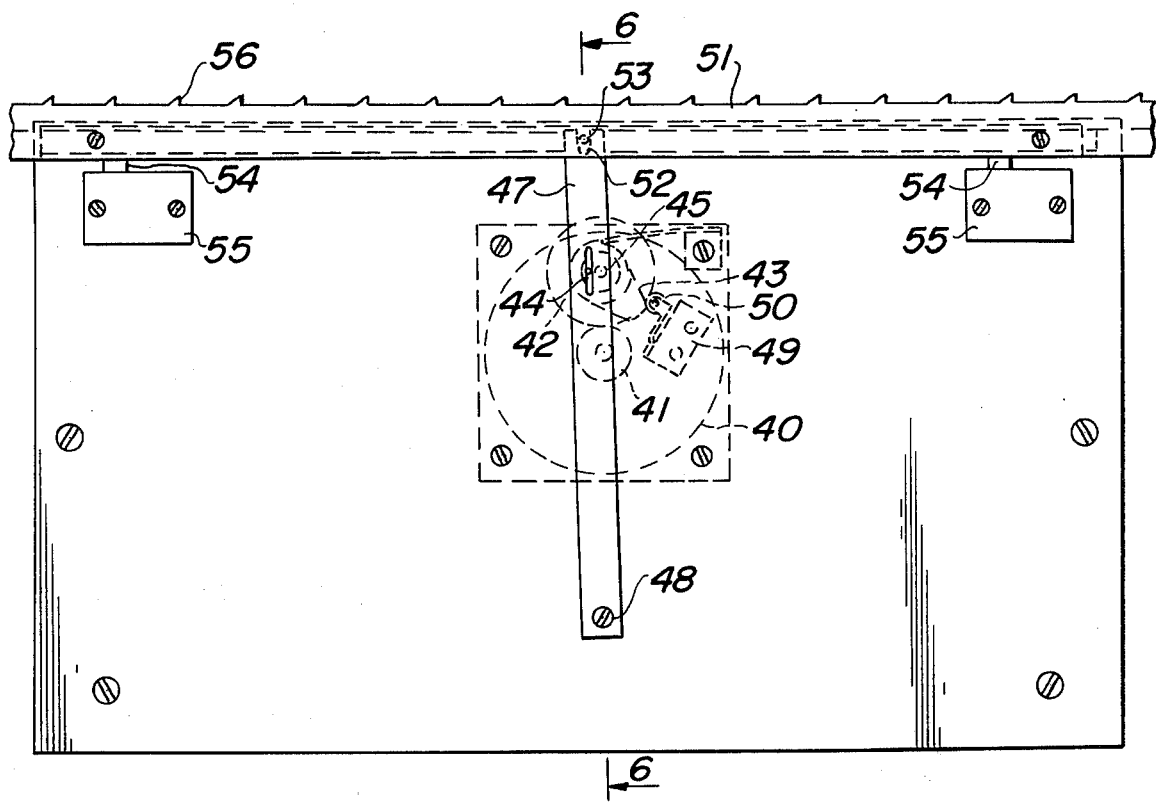
Figure 6:
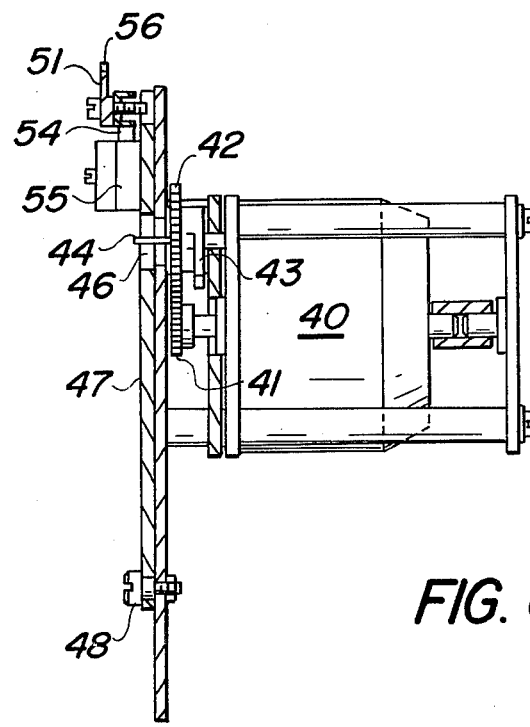
Figure 7:
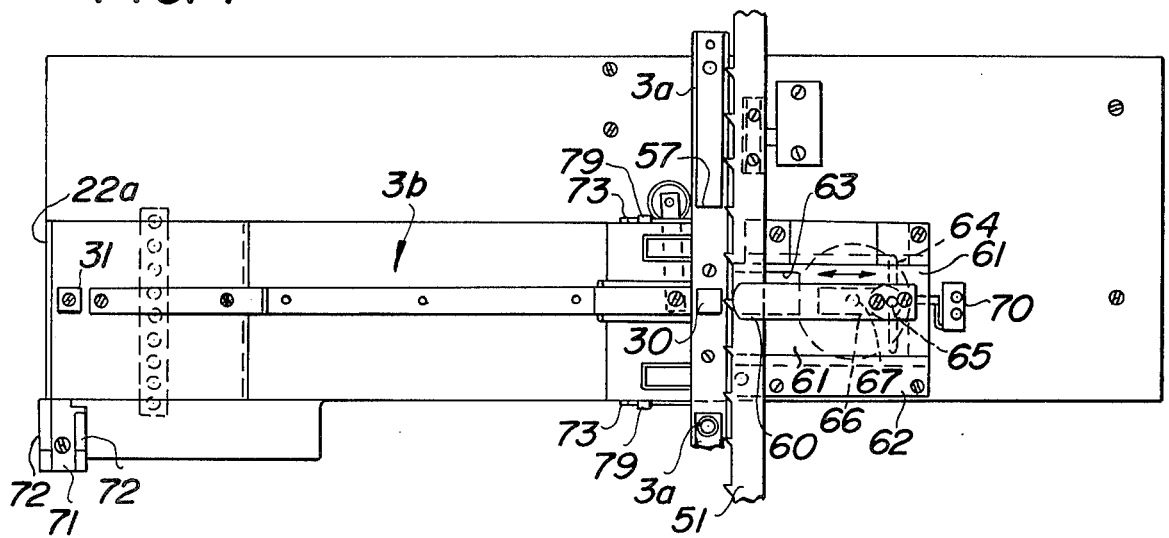
Figure 8:
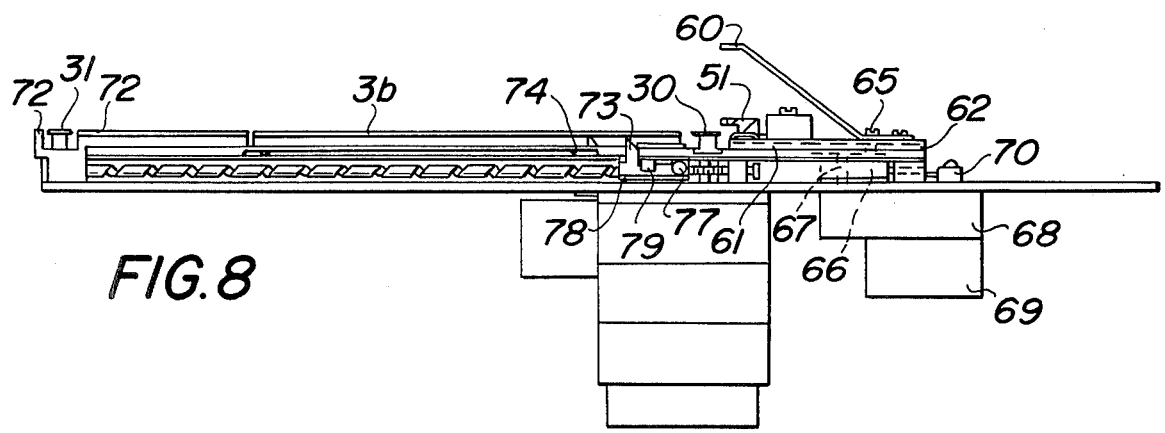
Figure 9:
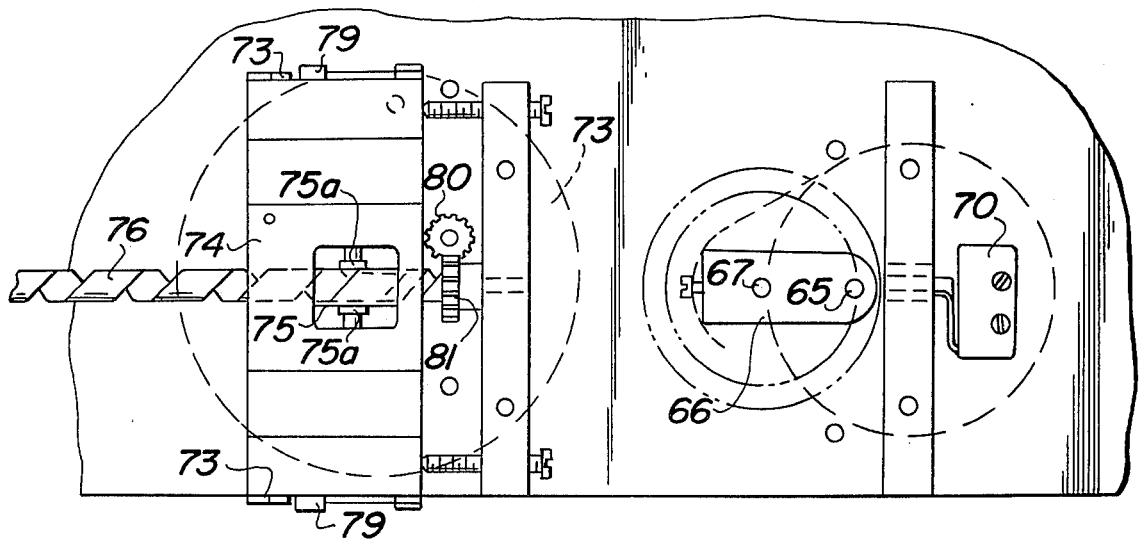

In the drawing, which is illustrative of the invention:

FIG. 1 is a plan view of the general assembly of an instrument employing the transport system of the present invention, FIG. 1a is an enlarged end view of a track or rail taken in the direction of the arrow 1a in the upper left-hand corner of FIG. 1, FIG. 1b is an enlarged perspective view of a junction guide post, FIG. 2 is a side elevation of a test tube holder or rack of the present invention, FIG. 3 is an end elevation of the holder, FIG. 4 is a bottom view of a plastic insert for elastically gripping test tubes in the holder, FIG. 5 is an enlarged plan view showing one section of the means for advancing the holder longitudinally along the main rail or trackway, FIG. 6 is a section along line 6—6 of FIG. 5, FIG. 7 is a plan view showing a junction in the main rail or track where it intersects a branch track and means for laterally shifting a holder from the longitudinal path along the main rack or track to a lateral or transverse path along the branch rail or track, FIG. 8 is a side elevational view of the structure shown in FIG. 7 with parts in cross-section, and FIG. 9 is a plan view somewhat enlarged corresponding to the plan of FIG. 7 except that it shows the substructure after removal of the rail or track, the plate supporting it, and everything therebove.

FIG. 1 is a top view of a transport arrangement in an instrument wherein a guide rail 3 extends from a loading end (at arrow 1a) of a supply ramp 4 to the discharge end thereof at 5.

The end view (and transverse section) of the rail 3 (see FIG. 1a) shows that it consists essentially of an upright but squat T having an upper section or strip wider than the lower section or strip so that both outer lateral edges of the upper strip overhang the lower section, preferably by an extent that is the same on both sides of the rail the full length of rail 3. The rail may be secured, as by screws 6, to a flat supporting plate, bed, or platform 4 that in this instance serves as a supply ramp to another rail 3a which may for convenience be called a main railway arranged to guide the test tube holder perpendicularly with respect to the railway 3.

As shown in FIGS. 2–4, the test tube holder has a generally rectangular integral body or frame with end walls 7, a top wall 8, and a base 9. The overall general shape or outline of the holder is that of a generally rectangular parallelepiped. Between the end walls 7, a plurality of upstanding webs 10 and intervening cylindrical passages 11 are adapted to receive test tubes, e.g., from the open upper ends thereof. The passages 11, which serve as receptacles are equidistantly spaced in the row thereof and the distance from the center of each end receptacle to the nearest end of the holder is half the spacing between centers of the receptacles so that the distance between the last receptacle in one holder and the first receptacle in the next contiguous holder moving longitudinally in tandem on a rail is the same as the spacing between adjacent receptacles in each holder.

The upper part of the base 9 is provided with recessed areas 12 along each side of the holder and these recessed areas leave intervening ribs or webs 13 the vertical center lines of which are spaced apart the same distance as the center lines of the receptacles 11. A channel extends longitudinally through the entire lower portion of the base 9. As shown in FIG. 3, this channel is open to the bottom of the base 9 and laterally defined by opposed walls which are provided with groove means comprising opposed longitudinal grooves, the lower pair of which 15 are adapted to cooperate with and slidably embrace, interlock with, or engage a T-rail, such as rail 3 hereinabove described whereby these grooves constitute guideways that allow the holder to be slid longitudinally of such a rail. Two ridges 14 extend inside each of the outer walls of the base 9 the full length thereof thereby providing the longitudinal recesses or grooves 15 adapted to receive the lateral edges of a T-shaped rail such as the rail 3 or 3a mentioned hereinafter. The groove means 15 interlocks with the lateral, overhanging edges of the upper portion of the rail as the holder slides lengthwise of the rail so that during such sliding the holder is held upright on the guideway, and it cannot be lifted off the rail.

As shown in FIG. 2, a transverse channel open to the bottom of base 9 is also provided extending through both sides of the base structure at right angles to the longitudinal channel. This channel has slot means, e.g., two opposed lateral grooves or recesses 16 at the same level as the grooves 15 in the longitudinal channel and adapted to cooperate with and slidably engage the lateral edges of a rail, such as rail 3. The slot means 16 interlocks with the lateral edge portions of the upper portion of the rail, e.g., rail 3, as the holder slides laterally the length of such a rail. During such sliding the holder is held upright on the guideway, and it cannot be lifted off the rail. It is by virtue of this transverse channel or guideway that the holder can be moved along the rail transversely as well as longitudinally.

The cylindrical receptacles 11 of the holder are adapted to receive test tubes in a disposition such that they form a row having center lines in a common plane the length of the holder. The groove means in the longitudinal channel in the base of the holder also comprises an upper pair of grooves forming a longitudinal slot just above the upper ridges 14. This pair of grooves or slot is adapted to receive a plastic insert 19 (FIG. 4) having a plurality of gripping means. This insert has a plurality of elastically flexible arms extending in pairs from one edge of the insert and define essentially circular openings which are somewhat smaller in diameter than the test tube to be inserted so that a given pair of the elastic arms will grip the test tube releasably when the test tube is pushed down into any one of such openings. To provide locating means, the last pair of elastic arms shown at the right of FIG. 4 are somewhat larger so that they can extend into two openings 20 formed in the base 9 (FIG. 2) structure and thereby allow the insert to be positioned definitely with each opening between pairs of arms located in alignment with each of the test tube receptacles 11. It is these elastic arms that allow the gripping of a test tube therein, allow push rods beneath the holder to push the test tubes upwardly to positions above the holder and also allow, because of the flexibility of the pairs of arms, the test tubes to be forced downwardly so that they partially protrude beneath the holder.

Further in FIG. 1, the holders containing test tubes may be placed in the supply ramp 4 by using the transverse slot of the holder so that it can be slid laterally down the rail with as many others as are desired to be placed in the supply rack. A suitable weight (on wheels) may be placed behind the last holder and the ramp 4 may be inclined from the horizontal so that the weight gravitationally urges the racks against each other along the rail 3 to the discharge end 5 of the supply ramp 4. The rail 3 terminates near the discharge position 5 and there is a gap between the end of rail 3 and a junction post 21. A barrier or stop 22 is fixed just beyond the post 21 with a similar gap therebetween (see also FIGS. 1a and 1b) and limits the travel of the row of holders moving beyond the discharge end 5 so that the foremost holder in such a row is stopped (by the barrier 22) in a position where it straddles the junction post 21.

The junction post (see FIG. 1b) is a knob having an upper portion that is a square in plan view and a lower supporting section that is a square concentric with the upper square but having smaller sides than the top so that one pair of parallel sides of the top may serve as a guideway or rail with respect to the transverse channel slot means 16 of the holder and the other pair of sides may serve as a guideway or rail with respect to the longitudinal channel grooves 15 of the holder, or vice versa. In the case of the junction post 21 located just beyond the discharge end of the loading ramp 4, the holders move laterally along the rail 3 and the transverse channel grooves 16 in the side walls of the holder embrace or engage the sides of rail 3 and the foremost holder is pushed over the narrow space or gap between the terminus of rail 3 and the adjacent side of post 21 in alignment with the rail. A similar gap or space is located between the far side of the post and the barrier 22. The thickness of these gaps correspond to the thickness of the lateral walls of the base 9 of a holder so that the foremost holder in straddling position over the post is slidable with respect to the post at right angles to the direction of approach thereto. The junction post 21 is secured to a flat supporting bed plate which has no obstruction on either side of the post for a sufficient distance to allow lateral movement of the foremost holder onto ramp 4 over the post without interference.

Another rail 3a, identical in construction to rail 3, is mounted in alignment with the post 21 so that movement of the holder to the right as viewed in FIG. 1 brings the grooves 15 in the longitudinal channel of the holder in guiding relationship with the rail 3a.

The way or rail along which the holders are moved longitudinally, that is, lengthwise is for convenience herein termed a "main way" or a "subsidiary way" when such a way is offset from and parallel to the main way whereas the adjoining ways or rails perpendicular to such a main way or subsidiary way and along which the holders move laterally either toward or from the main way or subsidiary way are herein termed "branch" ways or rails. One noteworthy characteristic of the trackway system of the present invention is that a junction between a branch way and either a main way or a subsidiary way perpendicular to the former requires a space or break in the rail of the main or subsidiary way slightly longer than the length of a holder and occupied by a junction post located in the break at a position corresponding to the position of the transverse channel slot means 16 along the length of the base 9 of the holder. The rail of the branch way ends alongside the break of the main or subsidiary channel and is substantially perpendicular to it. This construction allows the lateral shift of a holder (with respect to a branch way or rail) either onto a main way as at the junction post 21 in the main way comprising rail 3a or off the main way at a subsequent break in the rail as hereinafter described.

After the holder comes into straddling position over the junction post 21, it is moved in slidable engagement in respect to such post. Means is provided for moving the holder longitudinally with respect to the junction post onto rail 3a spaced just beyond the position occupied by the holder as it first reaches its position in engagement with the post 21. Means for advancing the holder longitudinally is shown as a toothed rack 25 which oscillates back and forth and thereby provides a stepping advance of the holder longitudinally of the rail, the increment of motion being made that of the spacing between receptacles in the holder.

As one holder is moved out of its position in front of the supply ramp, the entire supply of holders on such ramp is urged forward so that the leading holder takes position over the junction post 21 in readiness to be advanced by the longitudinal advancing means 25 immediately after the preceding holder has been forwarded. The advance is stepwise. The longitudinal advance means moves the holders stepwise from the supply ramp to the next position which in this instance is a transfer stage at 26. In this position, the test tube holder which may contain a row of empty clean test tubes passes under the tip or nozzle of a transfer pipette to receive a measured amount of a sample liquid therefrom and means may be provided to elevate (and then lower after transfer) each test tube within the holder in succession as the test tube comes under the pipette. A hole in the rail 3a at 26 allows a vertical rod to enter the bottom of each test tube receptacle and lift the test tube therein to an upper position with its mouth under the tip. After transfer action, the test tubes are each lowered back into the same receptacle in the holder and proceed to the next step of operation. Again, a step-advancing means such as a toothed rack may be provided along the track to forward the holders longitudinally thereof.

From this stage forward, the general assembly as shown in FIG. 1 involves the forwarding of the holders along a main rail or track to a stage wherein a reagent or other material may be added and mixed or vortexed with whatever happens to be in the test tube. This addition may be accomplished as the test tubes proceed through an addition stage 27 alongside the track and alongside a pipette console 28. This stage may also comprise equipment for mixing the materials within the test tube after addition of the reagent or the like, such as by vortexing. From this stage, the holders may proceed to the next position 29 where each holder in succession proceeds over a junction post 30 where the holders may be shifted laterally off the main way 3a onto a branch rail 3b by means of the lateral shifting mechanism at 31. This lateral shifting means operates intermittently so that when the transverse T-shaped channel slot means 16 of a holder is disposed over the post 30, the holder is pushed onto the track 3b extending at right angles thereto. As shown in the drawing, the holders which are forced onto rail 3b eventually reach a barrier 22a and straddle a junction post 31a adjacent the entrance to a centrifuge 32a. A pushing device 33 is adapted to push the holder straddling the junction post 31 into the centrifuge when it is stopped and in position to receive the holder. On the other side of the centrifuge, there is a mechanism 34 for reaching into the centrifuge, gripping the holder therein, and withdrawing it onto the table or platform 35 in straddling position over a junction post 36 at which position the holder is released by the gripping device 34 and is adapted to be shifted laterally by the mechanism 37 (similar to 31) onto the rail 3c.

FIG. 1 provides for the moving of a test tube holder laterally from the longitudinal guideway 3a onto the transverse guideway 3b from which it is supplied to a centrifuge and after centrifuging is discharged on the other side to a junction post 36, and laterally forced onto trackway or rail 3c. The holders proceeding along the main trackway 3a past the addition stage may instead be moved longitudinally to other devices such as to the entrance to an incubator wherein a suitable lateral shifting device moves the test tube holder laterally from that trackway (after being passed over a junction post) to a position between two travelling belts so that the two belts engage the ends of the holders and move the holder or holders laterally between opposed courses of the belts over a hot liquid bath, such as water. Means may be provided for pushing the tubes down in the holders so that they partially protrude beneath the bases thereof and are partly immersed in the liquid bath, the elastic gripping means 19 (FIG. 4) serving to hold the tubes in a lowered position thereof. Other devices may be provided in the instrument including a photometric device to which the holders containing the test tubes are diverted by way of a suitable trackway of the type described hereinbefore.

Besides the lateral diverting means 37 being essentially similar to that at 31, supplementary driving means of the same type mentioned hereinafter in respect to rail 3b may be provided for rail 3c which discharges laterally onto a junction post on a subsidiary railway having a rail 3d along which the foremost holder may be moved stepwise to the transfer stage 26 at which a measured amount of liquid, e.g., the supernatant is transferred by pipette to an empty tube on rail 3a. From this stage, the holder(s) on rail 3d proceed to the opening 99 in the supporting table or platform and fall into a waste or salvage receptacle for discard or salvage. Advancing rack means 25a (similar to 25) moves the holder to the left in stepwise fashion.

As disclosed in the preceding description, the first junction post 21 serves as a discharge station for the foremost holder of any number thereof provided on the supply ramp 4. The means 25 for advancing the holders longitudinally in succession from this discharge position is shown in FIGS. 5 and 6. The advancing means for advancing the holders stepwise longitudinally along the main rail or track may extend from a position alongside the discharge end 5 to the first stage such as the transfer stage 26. Separate such step-advancing means may be provided along individual sections of the longitudinal trackway 3a, the length of the advancing means along any portion or section of the path being dependent on the length of the section. FIG. 5 shows a plan view and FIG. 6 a sectional view of one such stepping advance mechanism. As shown there, a motor 40 drives a pinion 41 which drives a gear 42 provided with a cam 43 and a pin 44 eccentric to the axis 45 of the gear 42. The pin 44 extends upwardly into a slot 46 in an oscillating bar or arm 47 pivoted at 48. A microswitch 49 has a switch element 50 adapted to be actuated by the cam 43 to interrupt the motion of the bar 47 at the end of each revolution which serves to advance the rack 51 and the holder engaged thereby one step. The oscillating bar is provided with a slot 52 at one end and a pin 53 attached to the rack 51 extends into the slot 52. A pair of rods 54 are attached to the rack on either side of the arm 47 and extend into suitable means, such as grooves in cams in the casings 55 whereby during motion of the rack 51 to move the teeth to the right as in FIG. 5, the means 55 urges the rack and its teeth 56 into engagement with the ribs 13 of the test tube holder(s) and moves the holder(s) to the right therealong, whereas on the return stroke to the left, the rack is retracted out of engagement with the holder(s).

LATERAL DIVERTING MEANS

FIGS. 7–9 show an embodiment of means for diverting a holder laterally from a pathway on which it has been travelling longitudinally over a guide rail or track 3 at a point where such track is interrupted by a space the length of a holder and provided with a junction post. While such diverting means may be used at any position along a track from which it is desired that the holders be diverted laterally off a track along which the holders had previously been advancing longitudinally, the particular system shown in FIGS. 7–9, is concerned with the particular juncture post 30 in FIG. 1. In FIG. 7, for example, the longitudinal rail 3a is interrupted at the position shown and a space adapted to accommodate the length of a holder is provided between the end of such trackway and the beginning 57 of the next section of the trackway 3a. As shown in FIGS. 7–9, a holder that comes into position with its slotted transverse guideway 16 (FIG. 2) in alignment with the junction post 30 is in position to be laterally diverted from the longitudinal trackway 3a to the trackway 3b at right angles to the first direction. The cross-section of the toothed rack 51 is shown in FIG. 8 and a lateral diverting pusher 60 is secured to a slide plate 61 mounted within the upper surface of a stationary guide member 62 providing a guideway for movement of the plate 61 back and forth in the direction of the double-headed arrow shown in FIG. 7. The movable plate is provided with an aperture 63 which allows it to move relative to the junction post without interference with it. This movable plate is provided with a slot 64 into which a pin 65 extends. The pin is at the end of an arm 66 secured to the output shaft 67 of a reducing gear in a casing 68 driven by a motor 69. A microswitch 70 controls actuation of the motor and opens the motor circuit to stop the motor when the arm 66 comes to the position shown in FIGS. 7–9.

SUPPLEMENTARY DRIVING MEANS FOR A BRANCH RAIL

The movement of slide 61 (with the pusher element 60 to the left as viewed in FIGS. 7 through 9) shifts the test tube holder from the junction post 30 laterally onto the rail 3b to a position just beyond the two pivoted latch members 73 disposed on each side of a carriage 74 in the form of a plate or tray having an internally threaded sleeve 75 surrounding and engaging a rotatable screw shaft 76. The sleeve is secured against rotation by or about shaft 76 by suitable jaws 75a on the carrier 74 (see FIG. 9). The latch members 73 are pivotally mounted on the tray on axes 77 and are normally urged upwardly by leaf springs 78 into the position shown in FIG. 8 against detent means on each side of the tray, each detent means having a portion 79 extending downwardly alongside the respective latch member to serve as a guide therefor in its pivotal motion. As each test tube holder passes beyond the latch members, the latter spring back upwardly behind the holder. When the desired number of holders are shifted in succession from the track 3a onto track 3b, the motor 73 is actuated to rotate the screw 76 through worm gear 80 and gear wheel 81 and move the carriage 74 to the left as viewed in FIG. 8, the latch members serving to push the test tube holders along rail 3b until the foremost holder reaches the discharge end thereof, its base laterally abuts against the stop or barrier 22a (FIG. 7), and this holder comes to a stop on the junction post 31, from which it is moved by a pusher 33 (FIG. 1) longitudinally through a suitable guideway 71 between upstanding lateral guide edges 72.

The screw drive means just described aids in moving a plurality of holders equal to the number needed to charge the positions in the centrifuge into position against barrier 22a while leaving the entry section of rail 3b available to receive additional holders back of the carriage 74 until the centrifuge is loaded at which time, the screw is reversed, bringing the carriage 74 back to the starting position shown in FIGS. 7 to 9, the latch members being forced downwardly under the holder which the carriage and latches must pass under. The centrifuge and loading devices are disclosed in a copending U.S. application for patent Ser. No. 595,954, filed July 14, 1975 in the hands of a common assignee.

The drawing shows an analytical device having a plurality of service stations to which containers, e.g., test tubes, in holders are conveyed along a trackway or railway system, of simple "monorail" construction, having branch rails at right angles to main or subsidiary rails, and holders are used which have cooperating guide means in the base thereof to allow lateral shift of a holder to or from one main or subsidiary way from or to branch ways which are disposed at right angles to, and adjacent, junctions in the former ways. The rails mentioned above in such ways, 3, 3a, 3b, 3c, and 3d, are all of the construction shown in FIGS. 1, 1a, and 1b. The railway system may be provided in other stages to direct the holders to other service stations in the analytical device.

The guide rail structure of the present invention cooperates with the base of the holder to maintain the holder in its upright position and prevent it from being lifted deliberately or accidentally while it slides along the main, subsidiary, or branch rails whereby it can be shifted from or to a way on which it travels longitudinally to or from, respectively, a way on which it moves laterally, the terms "longitudinally" and "laterally" herein referring to the dimensions, i.e., the length of the holder. The "rail" system of the present invention provides stepwise movement along defined paths to one or more service stations in an analytical device, maintains the holders for test tubes and the like in upright positions, prevents accidental upsetting or lifting of the holders off the rail. It also provides lateral branch ways capable of storing a plurality of holders in readiness to be supplied to a particular servicing device, e.g., a centrifuge.

It is to be understood that the railway system of the present invention is not to be limited to the particular sequence of service stations described herein, but is intended to embrace many other systems of analytical servicing steps, in any desired sequence thereof.

We claim:

1. A holder for a plurality of test tubes adapted for manual and/or automatic transport to one or more service stations on a guideway system of an analytical device, comprising a body or frame having a base, a plurality of equidistantly spaced receptacles arranged in a row lengthwise of the holder and extending from the base to the top of the body, a longitudinal channel in the base extending the full length of the holder, open to the bottom of the holder along its entire length, and laterally defined by opposed inside surfaces of the sidewalls of the base, the channel having a guide structure comprising opposed groove means formed in said opposed inside surfaces of the sidewalls of the base, said groove means receiving lateral edges of a guide rail of the guideway system in the analytical device whereby the holder is maintained upright on said guide rail, said guide structure permitting lengthwise sliding of the holder on the guide rail longitudinally of the latter.

2. A holder according to claim 1 having a transverse channel through the base extending at right angles to the longitudinal channel, said transverse channel being open to the bottom of the holder and having a guide structure in and extending through the sidewalls of the base adapted to cooperate with a guideway of the device to maintain the holder upright and slidable laterally on the guideway.

3. A holder to claim 2 in which the transverse channel guide structure comprises a slot means extending through the longitudinal sidewalls of the base.

4. A holder according to claim 1 having a plurality of lateral formations, comprising ribs or webs, which are engaged by means, adjacent a guideway for the holder in the device, for moving the holder lengthwise along the guideway.

5. A holder according to claim 4 wherein the holder has a plurality of lateral vertical ribs spaced apart along the holder the same distances as the receptacles.

6. A holder according to claim 1 having a longitudinal slot in the base above the groove means, and an insert having a plurality of flexible arms extending in pairs from one edge of the insert and defining essentially circular openings, said insert being so positionable in said slot, that said essentially circular openings align with the receptacles in the holder.

7. A guideway system for transport of test tube holders in an analytical instrument for servicing a plurality of test tubes at a plurality of stations thereof, the system comprising at least two rails on a supporting table or platform, at least one thereof extending at right angles to the other, and means at the junction between the two rails to allow a holder to be shifted laterally from one rail to the other, said rails having a cross-section shape of a T, and each holder having a guide structure in a base thereof, said guide structure having opposite grooves into which overhanging lateral portions of the rail extend so as to prevent lifting of the holder off the rail.

8. A test tube holder having a body or frame, a channel formed in and open to the bottom of the body, a plurality of receptacles extending from the channel to the top of the body arranged in a row extending between the ends of the body, and groove means in the channel, said groove means receiving lateral edges of a guide rail in an analytical device in which the holder may be used, the holder slidingly engaging said guide rail in such manner that the holder is maintained upright on and cannot be lifted off from said guide rail.

9. A holder according to claim 8 in which a transverse channel is also formed in the bottom of the holder with guide means therein extending at right angles to the guide means of the first mentioned channel.

10. Analytical equipment comprising at least one service station, a supporting table, a guideway system thereon having a main way having a rail of T-shaped cross-section and at least one branch way at right angles to the main way having a rail of T-shaped cross-section terminating adjacent the main way, a junction post in the main way adjacent the end of the rail in the branch way, a test tube holder having a base in which a longitudinal channel extends the full length of the holder, said channel being laterally defined by opposed inside surfaces of the sidewalls of the base, the channel having a guide structure comprising opposed groove means formed in said opposed inside surfaces of the sidewalls of the base, said groove means receiving lateral edges of the T-shaped rails, said guide structure permitting lengthwise sliding of the holder on the rail, and a transverse channel through the base extending at right angles to the longitudinal channel, said channel being open to the bottom of the holder and having a guide structure in and extending through the sidewalls of the base, said guide structure receiving the lateral edges of the T-shaped rail and permitting lateral sliding of the holder on the rail and means for running the holder along the rail.

11. Equipment according to claim 10 comprising means for laterally shifting a test tube holder with respect to two ways perpendicular to each other at a junction therebetween.

12. Equipment according to claim 10 comprising means for lengthwise advancing a holder stepwise along a main way.

13. Equipment according to claim 10 comprising means for lengthwise advancing a holder stepwise along a main way, means for laterally shifting a test tube holder with respect to two ways perpendicular to each other at a junction therebetween, and means for advancing holders, laterally shifted onto a branch way, laterally on such way to a detention stop at the end of the way with the foremost of the holders straddling a junction post whereby the foremost holder is in a position to be moved lengthwise away from the branch way.

* * * * *